US006501007B1

(12) United States Patent
Ashikari et al.

(10) Patent No.: US 6,501,007 B1
(45) Date of Patent: Dec. 31, 2002

(54) METHOD OF DWARFING PLANTS

(75) Inventors: Motoyuki Ashikari, Ibaraki (JP); Atsushi Yoshimura, Fukuoka (JP); Masahiro Yano, Ibaraki (JP); Takashi Matsumoto, Ibaraki (JP); Takuji Sasaki, Ibaraki (JP); Jianzhong Wu, Ibaraki (JP); Kimiko Yamamoto, Ibaraki (JP)

(73) Assignee: National Institute Of Agrobiological Sciences, Ibaraki (JP)

( * ) Notice: Subject to any disclaimer, the term of this patent is extended or adjusted under 35 U.S.C. 154(b) by 0 days.

(21) Appl. No.: 09/335,586

(22) Filed: Jun. 18, 1999

(30) Foreign Application Priority Data

Jun. 19, 1998 (JP) ............................................ 10-189773

(51) Int. Cl.$^7$ ........................ C12N 15/09; C12N 15/29; C12N 15/82; A01H 5/00

(52) U.S. Cl. ...................... 800/290; 800/285; 800/286; 800/278; 800/298; 800/295; 800/293; 435/69.1; 435/468; 435/419; 435/430; 536/23.6; 536/24.5

(58) Field of Search ................................ 800/290, 286, 800/278, 298, 295, 293, 285; 435/69.1, 468, 419, 430; 536/23.6, 24.5

(56) References Cited

U.S. PATENT DOCUMENTS 5,052,543 A * 10/1991 Firoozabady et al. ....... 800/294

FOREIGN PATENT DOCUMENTS

WO    WO 9741152    11/1997

OTHER PUBLICATIONS

Seo et al. Accession No. L28001, Sequence Search Results, p. 3, Jun. 1995.*
Evans et al. Biochemistry Society Transactions, vol. 20, p. 344S, 1992.*
Napoli et al. The Plant Cell, vol. 2, pp. 279–289, Apr. 1990.*
Sandler et al. Plant Molecular Biology, vol. 11, pp. 301–310, 1988.*
Kuipers et al. Mol. Gen. Genet., vol. 246, pp. 745–755, 1995.*
Bird et al. Biotechnology and Genetic Eng. Rev. vol. 9, pp. 207–227, Dec. 1991.*
Smith et al. Science, vol. 334, pp. 724–726, Aug. 1988.*
Kossmann et al. Progress in Biotech.–10, Proc. Int. Conf. pp. 271–278, Apr. 1995.*
Ashikari et al., "Genetic Analysis of a D1 Chimeric Rice Plant," *International Rice Research Notes* 22:12–13 (1997).
Fujisawa et al., "Suppression of the Heterotrimeric G Protein Causes Abnormal Morphology, Including Dwarfism, In Rice," *Proceedings of the National Academy of Sciences of the USA* 96:7575–7580 (1999).

Ishikawa et al., "Molecular Cloning and Characterization of a CDNA for the Alpha Subunit of a G Protein from Rice," *Plant and Cell Physiology* 36:353–359 (1995).
Kamada et al., "Transgenic Tobacco Plants Expressing RGP1, A Gene Encoding A Ras–Related GTP–Binding Protein From Rice, Show Distinct Morphological Characteristics," *Plant Journal* 2:799–807 (1992).
European Search Report.
Akemine M. et al., Nihon Gakujutsukai Houkoku (Japan Science Council Report), vol. 1, pp. 308–314, 1925.
Kikuchi Y. et al., Kagaku To Seibutsu (Chemistry and Biology), vol. 30, No. 2, pp. 112–118.
Nakayama K., Shinsyudai Bunrigakubu Kiyou (Journal of Faculty of Liberal Arts and Science Shinsyu University) vol. 4, pp. 1–31, 1954.
Takahashi M. and Takeda K., Hokudai Nougakubu Houbun Kiyou (Memories of the Faculty of Agriculture Hokkaido University), vol. 7, No. 1, pp. 32–43, 1969.
Hirashima et al., "Shinseikagaku Jikken Kozs (New Biochemistry Experimentation Lectures) 2, Kakusan (Nucleic Acids) IV, Idenshi No Fukusei To Hatsugen (Replication and Expression of Genes)", Nihon Seikagakukai Hen (The Japanese Biochemical Society), Tokyo Kagaku Dozin Chapter 7, pp. 319–347, 1993.
Koizumi M. and Otsuka E., Tanpakushitsu Kakusan Kohso (Nucleic acids, Protein and Enzyme), vol. 35, No. 13, pp. 2191–2200, 1990.
Kinoshita T., Rice Genetics Newsletter, vol. 12, p. 9, pp. 30–32, 1995.
Nagao S. and Takahashi M., Journ. Facul. Agr., Hokkaido Univ., vol. 53, Pt. 1, pp. 73–130, 1963.
Iwata N. and Omura T., Japan J. Genetics, vol. 51, No. 2, 135–137, 1976.
Suge H. and Murakami Y., Plant & Cell Physiol., vol. 9, pp. 411–414, 1968.
Mitsunaga S. et al., Theor. Appl. Genet., vol. 87, pp. 705–712, 1994.
Seo H.K., et al., Plant. Mol. Biol., vol. 27, pp. 1119–1131, 1995.

(List continued on next page.)

*Primary Examiner*—Phuong T. Bui
*Assistant Examiner*—Medina A. Ibrahim
(74) *Attorney, Agent, or Firm*—Fish & Richardson

(57) ABSTRACT

A method of dwarfing plants comprises controlling the expression of the genes involved in the dwarfism of the plants is provided. A molecule to be utilized for dwarfing plants is also provided. A single gene that causes the d1 mutation, which results in the dwarf abnormality of rice, was identified and isolated from a vast chromosomal region by the map-based cloning technique. This method enables, for example, creating ornamental plants and agricultural products with new commercial values, and therefore is useful especially in the areas of agriculture and horticulture.

8 Claims, 4 Drawing Sheets

OTHER PUBLICATIONS

Iwasaki Y. et al., Plant. Mol. Biol., vol. 34, p. 563, 1997.
Southern E.M., J. Mol. Biol., vol. 98, pp. 503–517, 1975.
Saiki R.K. et al., Science, vol. 230, pp. 1350–1354, 1985.
Saiki, R.K. et al., Science, vol. 239, pp. 487–491, 1988.
Ecker, J.R. Davis, R.W., Proc. Natl. Acad. Sci. USA, vol. 83, pp. 5372–5376, 1986.
Van der Krol, A.R. et al., Nature, vol. 333, pp. 866–869, 1988.
Koizumi M., Nucleic Acids Res., vol. 17, No. 17, 1989.
Buzayan, J.M. et al., Nature, vol. 323, pp. 349–353, 1986.
Kikuchi Y. and Sasaki N., Nucleic Acids Res., vol. 19, No. 24, pp. 6751–6755, 1991.
Taira K. et al., Nucleic Acids Res., vol. 19, No. 19, pp. 5125–5130, 1991.
Dzianott, A.M. and Bujarski, J.J., Proc. Natl. Acad. Sci. USA., vol. 86, pp. 4823–4827, 1989.
Grosshans, C.A. and Cech, T.R., Nucleic Acids Res., vol. 19, No. 14, pp. 3875–3880, 1991.
Yuyama N. et al., Biochem. Biophys. Res. Commun., vol. 186, No. 3, pp. 1271–1279, 1992.
Osawa S. and Johnson, G.L., The Journal of Biological Chemistry, vol. 266, No. 8, p. 4673–4676, 1991.
Bustos, M.M., et al., The EMBO Journal, vol. 10, No. 6, pp. 1469–1479, 1991.
Lelievre, J.M., et al., Plant Physiol., vol. 98, pp. 387–391, 1992.
Lam, E. and Chua, N.H., Science, vol. 248, pp. 471–474, 1990.
Gotor, C. et al., The Plant Journal, vol. 3, No. 4, pp. 509–518, 1993.
Yamamoto Y.T., et al., The Plant Cell, vol. 3, pp. 371–382, 1991.
Toki S. et al., Plant Physiol., vol. 100, pp. 1503–1507, 1992.
Churchill, G.A. et al., Proc. Natl. Acad. Sci. USA., vol. 90, pp. 16–20, 1993.
Umehara Y. et al., Molecular Breeding, vol. 1, pp. 79–89, 1995.

* cited by examiner

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
      (A) LENGTH: 380 amino acids
      (B) TYPE: amino acid (D) TOPOLOGY: linear (ii) MOLECULE TYPE: protein (xi) SEQUENCE DESCRIPTION: SEQ ID NO: 1:

```
Met Gly Ser Ser Cys Ser Arg Ser His Ser Leu Ser Glu Ala Glu Thr
 1               5                  10                  15

Thr Lys Asn Ala Lys Ser Ala Asp Ile Asp Arg Arg Ile Leu Gln Glu
            20                  25                  30

Thr Lys Ala Glu Gln His Ile His Lys Leu Leu Leu Leu Gly Ala Gly
            35                  40                  45

Glu Ser Gly Lys Ser Thr Ile Phe Lys Gln Ile Lys Leu Leu Phe Gln
        50                  55                  60

Thr Gly Phe Asp Glu Ala Glu Leu Arg Ser Tyr Thr Ser Val Ile His
65                  70                  75                  80

Ala Asn Val Tyr Gln Thr Ile Lys Ile Leu Tyr Glu Gly Ala Lys Glu
                85                  90                  95

Leu Ser Gln Val Glu Ser Asp Ser Ser Lys Tyr Val Ile Ser Pro Asp
            100                 105                 110

Asn Gln Glu Ile Gly Glu Lys Leu Ser Asp Ile Asp Gly Arg Leu Asp
            115                 120                 125

Tyr Pro Leu Leu Asn Lys Glu Leu Val Leu Asp Val Lys Arg Leu Trp
130                 135                 140

Gln Asp Pro Ala Ile Gln Glu Thr Tyr Leu Arg Gly Ser Ile Leu Gln
145                 150                 155                 160

Leu Pro Asp Cys Ala Gln Tyr Phe Met Glu Asn Leu Asp Arg Leu Ala
                165                 170                 175

Glu Ala Gly Tyr Val Pro Thr Lys Glu Asp Val Leu Tyr Ala Arg Val
            180                 185                 190

Arg Thr Asn Gly Val Val Gln Ile Gln Phe Ser Pro Val Gly Glu Asn
            195                 200                 205

Lys Arg Gly Gly Glu Val Tyr Arg Leu Tyr Asp Val Gly Gly Gln Arg
210                 215                 220

Asn Glu Arg Arg Lys Trp Ile His Leu Phe Glu Gly Val Asn Ala Val
225                 230                 235                 240

Ile Phe Cys Ala Ala Ile Ser Glu Tyr Asp Gln Met Leu Phe Glu Asp
                245                 250                 255

Glu Thr Lys Asn Arg Met Met Glu Thr Lys Glu Leu Phe Asp Trp Val
            260                 265                 270

Leu Lys Gln Arg Cys Phe Glu Lys Thr Ser Phe Ile Leu Phe Leu Asn
            275                 280                 285

Lys Phe Asp Ile Phe Glu Lys Lys Ile Gln Lys Val Pro Leu Ser Val
290                 295                 300

Cys Glu Trp Phe Lys Asp Tyr Gln Pro Ile Ala Pro Gly Lys Gln Glu
305                 310                 315                 320

Val Glu His Ala Tyr Glu Phe Val Lys Lys Phe Glu Glu Leu Tyr
                325                 330                 335

Phe Gln Ser Ser Lys Pro Asp Arg Val Asp Arg Val Phe Lys Ile Tyr
            340                 345                 350

Arg Thr Thr Ala Leu Asp Gln Lys Leu Val Lys Thr Phe Lys Leu
            355                 360                 365

Ile Asp Glu Ser Met Arg Arg Ser Arg Glu Gly Thr
370                 375                 380
```

(2) INFORMATION FOR SEQ ID NO: 2:

(i) SEQUENCE CHARACTERISTICS:
        (A) LENGTH: 1461 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: Coding Sequence
        (B) LOCATION: 91...1230

(xi) SEQUENCE DESCRIPTION: SEQ ID NO: 2:

```
GACGTCAACG TGCTTCCTGG AAAGAGAGAG GCTCAGGCAT GAGAGCATAC CTCTAAAATA          60

ATGTCCGTGC TTACCTGTGT GCTTGATAAC  ATG GGC TCA TCC TGT AGC AGA TCT        114
                                  Met Gly Ser Ser Cys Ser Arg Ser
                                    1               5

CAT TCT TTA AGT GAG GCT GAA ACA ACC AAA AAT GCA AAA TCT GCA GAC          162
His Ser Leu Ser Glu Ala Glu Thr Thr Lys Asn Ala Lys Ser Ala Asp
         10                  15                  20

ATT GAC AGG CGA ATT TTG CAA GAG ACA AAA GCA GAG CAA CAC ATC CAC          210
Ile Asp Arg Arg Ile Leu Gln Glu Thr Lys Ala Glu Gln His Ile His
 25                  30                  35                  40

AAG CTC TTA CTT CTT GGT GCG GGA GAA TCA GGG AAG TCT ACG ATA TTT          258
Lys Leu Leu Leu Leu Gly Ala Gly Glu Ser Gly Lys Ser Thr Ile Phe
                 45                  50                  55

AAA CAG ATT AAG CTC CTT TTC CAA ACT GGC TTT GAT GAG GCA GAA CTT          306
Lys Gln Ile Lys Leu Leu Phe Gln Thr Gly Phe Asp Glu Ala Glu Leu
             60                  65                  70

AGG AGC TAC ACA TCA GTT ATC CAT GCA AAC GTC TAT CAG ACA ATT AAA          354
Arg Ser Tyr Thr Ser Val Ile His Ala Asn Val Tyr Gln Thr Ile Lys
         75                  80                  85

ATA CTA TAT GAA GGA GCA AAA GAA CTC TCA CAA GTG GAA TCA GAT TCC          402
Ile Leu Tyr Glu Gly Ala Lys Glu Leu Ser Gln Val Glu Ser Asp Ser
     90                  95                 100

TCA AAG TAT GTT ATA TCC CCA GAT AAC CAG GAA ATT GGA GAA AAA CTA          450
Ser Lys Tyr Val Ile Ser Pro Asp Asn Gln Glu Ile Gly Glu Lys Leu
105                 110                 115                 120

TCA GAT ATT GAT GGC AGG TTG GAT TAT CCA CTG CTG AAC AAA GAA CTT          498
Ser Asp Ile Asp Gly Arg Leu Asp Tyr Pro Leu Leu Asn Lys Glu Leu
                125                 130                 135

GTA CTC GAT GTA AAA AGG TTA TGG CAA GAC CCA GCC ATT CAG GAA ACT          546
Val Leu Asp Val Lys Arg Leu Trp Gln Asp Pro Ala Ile Gln Glu Thr
            140                 145                 150

TAC TTA CGT GGA AGT ATT CTG CAA CTT CCT GAT TGT GCA CAA TAC TTC          594
Tyr Leu Arg Gly Ser Ile Leu Gln Leu Pro Asp Cys Ala Gln Tyr Phe
        155                 160                 165

ATG GAA AAT TTG GAT CGA TTA GCT GAA GCA GGT TAT GTG CCA ACA AAG          642
Met Glu Asn Leu Asp Arg Leu Ala Glu Ala Gly Tyr Val Pro Thr Lys
    170                 175                 180

GAG GAT GTG CTT TAT GCA AGA GTA CGG ACA AAT GGT GTT GTA CAA ATA          690
Glu Asp Val Leu Tyr Ala Arg Val Arg Thr Asn Gly Val Val Gln Ile
185                 190                 195                 200

CAA TTT AGT CCT GTT GGA GAA AAC AAA AGA GGT GGA GAG GTA TAT AGG          738
Gln Phe Ser Pro Val Gly Glu Asn Lys Arg Gly Gly Glu Val Tyr Arg
                205                 210                 215

TTG TAT GAT GTA GGA GGC CAG AGG AAT GAG AGG AGA AAG TGG ATT CAT          786
Leu Tyr Asp Val Gly Gly Gln Arg Asn Glu Arg Arg Lys Trp Ile His
            220                 225                 230

CTT TTT GAA GGT GTT AAT GCG GTA ATC TTT TGT GCT GCC ATT AGC GAA          834
```

```
Leu Phe Glu Gly Val Asn Ala Val Ile Phe Cys Ala Ala Ile Ser Glu
        235                 240                 245

TAT GAT CAG ATG CTA TTT GAA GAT GAG ACA AAA AAC AGA ATG ATG GAG      882
Tyr Asp Gln Met Leu Phe Glu Asp Glu Thr Lys Asn Arg Met Met Glu
    250                 255                 260

ACC AAG GAA CTC TTT GAC TGG GTT TTA AAG CAA AGA TGT TTT GAG AAA      930
Thr Lys Glu Leu Phe Asp Trp Val Leu Lys Gln Arg Cys Phe Glu Lys
265                 270                 275                 280

ACA TCA TTC ATT CTG TTT CTC AAC AAA TTT GAT ATA TTC GAG AAG AAA      978
Thr Ser Phe Ile Leu Phe Leu Asn Lys Phe Asp Ile Phe Glu Lys Lys
                285                 290                 295

ATA CAA AAG GTT CCT TTA AGT GTG TGC GAG TGG TTT AAA GAC TAC CAG     1026
Ile Gln Lys Val Pro Leu Ser Val Cys Glu Trp Phe Lys Asp Tyr Gln
                300                 305                 310

CCT ATT GCA CCT GGG AAA CAG GAG GTT GAA CAT GCA TAT GAG TTT GTC     1074
Pro Ile Ala Pro Gly Lys Gln Glu Val Glu His Ala Tyr Glu Phe Val
                315                 320                 325

AAG AAG AAG TTT GAA GAG CTC TAC TTC CAG AGC AGC AAG CCT GAC CGT     1122
Lys Lys Lys Phe Glu Glu Leu Tyr Phe Gln Ser Ser Lys Pro Asp Arg
        330                 335                 340

GTG GAC CGC GTC TTC AAA ATC TAC AGA ACT ACG GCC CTA GAC CAG AAA     1170
Val Asp Arg Val Phe Lys Ile Tyr Arg Thr Thr Ala Leu Asp Gln Lys
345                 350                 355                 360

CTT GTA AAG AAG ACA TTC AAG TTG ATT GAT GAG AGC ATG AGA CGC TCC     1218
Leu Val Lys Lys Thr Phe Lys Leu Ile Asp Glu Ser Met Arg Arg Ser
                365                 370                 375

AGG GAA GGA ACT TGATTCAGAG CTAAGACTAG GTTGTAAGTC ACACAGGGAA GGTAA    1275
Arg Glu Gly Thr
            380

TTAGGACGGC GAGAGGAACA AGTTTCACA CTGTCACAGC TTTATCTGTT GTAATTCTTT    1335

TACACGTGGA CCATTGATTG ATCTTTTGGT TCTTACTGTG GGCTGTTCAG GTCTGTACCC   1395

TATTTTTTGT TCTCTAGTTA GCCATTGTGC AAATTTTCCT TGAATCAGAT TCTCTACCTG   1455

TTGTCT                                                              1461

(2) INFORMATION FOR SEQ ID NO: 3:

(i) SEQUENCE CHARACTERISTICS:
        (A) LENGTH: 8107 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO: 3:

GAATTCTCAT GTCTGTAACT TCATTTTTAA GCCATAGAAA TCTAGTTCCA TCCAAAACAC     60

CAAAACGGAT GGTGTTTTAC AGTAGCTTGT CATATGCTTT TAGGCGAGCT TACTAGTCTA    120

TTTTTCATAA TACTTTTTCA CAATTTTGAA AGGCCTAGGG AGTAATATTT AATGGTGCAA    180

AAGGGACGAG TTTTGAAACA TTTGTTTGTC GCAGAAGCAC CAGACCATTC TGATTGTTAT    240

TGTAAGCTGT AACATCAAAG TTTTGGCAGC AGGTTTTCAT GTGCTCTTAA GCGTTGGGGG    300

TTTGTTCCGT TTGGTTTTCA ACTGTATGCT AGCTTTCTCT ATTAGCCAAT GTAATGGCAG    360

TTGCAAAATC TGTTGTAGTG CAGGCGTGCA GCTAAATGCA GTATAGCTGA CTGTTAACTT    420

TAAGCTGATT GTCCCATGCA GTCCCAGTA AAAGGACAGT CAGGAATGAG TCTCATGGGT    480

CAATATATGG TGCAGACATG TCAGTAGGAT ATAGGAGTAT TACATTATAG TTTTTTCAGC    540

TTCAATAACG TTCATGTTAG CTTGTACATT GTATGGCAAC CCTTCCATAC TTGCGTTAGC    600
```

-continued

| | |
|---|---|
| ACAAAAGTTC ACCATGTTAG CTTGGCTTTA GATCAGTTTA AACTGTCCTT TAATAGCAAA | 660 |
| TTAATAATCC ATAAAATGAA ATTTTACTTC CACTGTTTAC CAGTGCTACT ACTGTTCTAC | 720 |
| CTCCAGCGTT CAACAGCTGA GAAACGTGAG GAGTCCAGCA CCAGCAGTAT CATTTACTGC | 780 |
| AATGCGAGAG AGATGTTCTC CGTTTCCTCC TTCACTGAGG CTTAGGAGTA GGAGGAGTAG | 840 |
| TAGTGATTTT TTCGTGTCGA CTTGTTTAAC ATTATCATTA ACACCATCAA GTGTCAATGC | 900 |
| CAGTAGGCTG CTGCTTCTAA TCATTTCTTC CTTCCCTCTT CTAACGCCAT TATCGTTTTA | 960 |
| TCTCACCTTG CATTTATGTT CAAGTGACCA TGGTTCTTGA CAGAAGCAGC CCTTGTTCTT | 1020 |
| TCCTGTCCCT TTGTTTGTTC AGTACGCTAT TATTCTCTTG GGTACTAGAC CTTGTATAAA | 1080 |
| CCGGTTGTGA AATCCTCAAT CAAATAAAAG TTAACTCGAA ATTTGTGGCC TGTTCCAAGT | 1140 |
| GTTTGGCAAA CCAATATGTA TATTATCCAC CCGATTATCT AATGGCAATA CAGTGCCTAA | 1200 |
| AATTCCTGCT TCCGGAGTCT TAAACTTTAC CCGAATCCAA TCTGGAAACC GAAAAGACAG | 1260 |
| CTGCTTAGCT GATGGCAAGT CACTGGGTAC ATTGATTTGT GTTAATTTTC AGTCCAATAA | 1320 |
| AACAGCGCAA AAATTGTAAG GGTGATCCCT CTTTAGTAAA GCCATGCATT CTGCAAACTC | 1380 |
| TGTTGCAATG CAAGCTGTAT CCTATATCCA GTGCCGATGA ACCAATTCTG TTTGCAGACT | 1440 |
| GTACCCTATC TCTACTCTAC AAGCCAACCA AAGGAAAGTG TTTGATCTGC AGTGGAATAC | 1500 |
| TAGCAGGTAT TCCACCATTT CAGGGTTGGG AGTGTGATTG ATATGCAGGA GATTGACATT | 1560 |
| GTGCAGAACA TTGGCCGTCA GCTGCCGCTG CCGTCGCCGG TGGTGTCGGT GAGAAAGCCC | 1620 |
| GGTGGTGGTG GTTGTGCCGG CGGCGAGGAG TGGCTGCAAC AGGATGGGCT GTTGTGCATG | 1680 |
| GGCGGATCAG CGGGTGGCTT ATGGCGGTGG CCACGCTGTT AGCCGGCGAC GGACCCGGCG | 1740 |
| GCGGCGTCCT TCACGAGGGA CGGCGCATGA TGATCCTGGA TAATTTCGAG ACTTCGGGCC | 1800 |
| GGCGTTCGTG CAAAGCCCAT ACATATTCTA CGCGCAACTG TCACGCACAA AAACGAAGTT | 1860 |
| TTTAGTACCA CATGGAAAAT CTATGACGAC TAACACCGGC ATAAAAGACG ACGCGCTCGC | 1920 |
| ATAGCGGGAG TTGGCAGTTT TCGGCTGCTG GAGAAAACGA GGTTTCTCCC TCGATCGAAT | 1980 |
| GGATGCAAAC ATCCTCCCGA CTTTGGCCCA CTAGGGAGGG AAGGTGTGAG TCACCCTGGG | 2040 |
| CTCCAGACGG CTGCGTCATG GAGCGAAGAG GACCAACCGA CACCCTTCTC CCCACCCATT | 2100 |
| GGCGAATGCC CTAGAGGTTT GGGCAACCGA CACCCTTCTC CCCACCTATT GACGAATGCC | 2160 |
| CTTGGGTTGA GATAGGAGTA GAGGGGAGTG AGGTCTTCTC CCCACCCATT GGCGAATGCC | 2220 |
| TTTGGGTTGA GATAGGAGTA GAGGGGAGTG AGGTCTTCTC CCCACCCATT GGCGAATGCC | 2280 |
| CTAGAGGTTT GGGCAACCGA CACCCTTCTC CCCACCCATT GGCGAATGCC CTAGAGGTTT | 2340 |
| GGGTTGAGAT AGGAGTAGAG GGGAGTGAGG TGGAAGAAGA TTGCTAGTTG GCTTGTGGGG | 2400 |
| TTCCACGTGG GCCCTGCACT GACTCAGCCA CCACGTTAAC AAAACCGGAA AGCAATACTA | 2460 |
| CCTTGGGATT AAAAGTGGTC CGTTTGCAAG ATTAGGGGTT CAGGGCCGTG TAAAACTCAA | 2520 |
| CGACAAGATA AGGGACCTTA GATGAACTTT TTTGGGAGAT GAGGCGCCTG TGCATATGAC | 2580 |
| CCATAGGCAG GCGACACCGC GGCAGAGCGG CGCTGCACGA CCTCCGCCTC CCCAATCCGT | 2640 |
| CCCGTCTCCT CGCCCGCCGC CCTCGACTCC CGTCTCCTCG CCTGCCGCTG GCGCCGATCT | 2700 |
| CCATCCTGCT AGCAGAGGTG GCGCCGGCGT CCTCCTGCTC CCGCCGCATT CGCATCCTAA | 2760 |
| TCCATCCCAT CCGGCCTCGG CCTCGAATTT CGTCTCCTCG CCCGCCGCTT GCGCCGATCC | 2820 |
| CATCCTGCGA GCAGAGGTGG CGCCCGGCGT CCTCCTTCCA CCGTATCGTA GCTCGCCGGT | 2880 |
| GAGCATCCCT CCCTACCCAC ACCTCATCAG GTATTCTGCG TTATCCCTCA AAAGTTTGG | 2940 |

```
GGGTTCAACC GAAACAGGGT TAGATCTGCC TCTGCCCAGC TCCACCTACT TTCAAGTTGT      3000

TAATTTTGAT TTCCGTTTTT AGCAGATGTA ATTTGGTTAT TGAATCTCAT CCAAACACCC      3060

TCAGAACGAA AAATGTAAGC TTACATAATT TGTACTCATC CAAACTTACA TAAATTTCTT      3120

AAGGAGAATC TAGACCACAA ACTACCCATA GTCACACAAA ATATCTTTTT ATCAAGGTAT      3180

TCTTATAAGT AATTTTAATT CCACAAAATT TTCTAAAGGA CATACTGTGA CACTTGGCAT      3240

GAATCTAATT TAACATTCTT TCTTTATCAG GTTATAAATT GAAACCATTG AACGTATTTT      3300

GTCTTCCCGT CCCTACAACA TTGTGATATA TCTGTAATAT TTAATATTT TTAATTTTAA      3360

AAATATTTAG ACTAATAATA TAGATATTTA ATTAGGTAAT TAATAAATTC AAATCAAATG      3420

TAGTTTGAAA TAAATAAACA AAATGATATA TGCCAAGTAC AATCTAATAT CGGGCATGAT      3480

TTTAGATGTA GTAGGTATTA TTCTGGAATA CTCCTCGTTG AAACATATGG AACGCATTTC      3540

CCTGAAAAAG GAAAATTTTT TGCCCCGACC CCTCGCACC AACCCCGTCG GATGTGAAGC      3600

CGACGCGCCA GATGGAGGCC AGCGGTGCCA ATGCGTAGGC CAATCGTGCC TCTGGGGAAA      3660

TCTTATCTCC CGGGGCCGGA CGGCTCCGCT CCACTTCCCT CCCCGAGTCA CTCAAACCAT      3720

CCAATCCCCC ACACTCCCTT CCCTTGCCCC CATTCCCCAC CGCCGCAAGG AAAAATATTG      3780

TTAATAAACA ATGATGTTGA TGTATTATTA ATAAACAATG ATATTGATGT ATTTCTAAAT      3840

ATTTTCACGT ATTATTTATT AAGTGTCAGT GATTGAAATG GATCCTGGTC GGAAATGAAT      3900

CCTGGTCGGA AAATGGTTAC TAATGTTTTT CCTTCATATA ATATTTCTGG ATATGTATAA      3960

CAATGTGGGT CAGCAATATT GAACTATGCA AACCATTACT CTGTACAATC TTTTCTTTTC      4020

AAATGCTGGC CACATTTCGC TCGAGCTTAC TGCTCATGTA TGCAGCTCAT GGATCCTGAG      4080

ATCTAGACGT CAACGTGCTT CCTGGAAAGA GAGAGGCTCA GGCATGAGAG CATACCTCTA      4140

AAATAATGTC CGTGCTTACC TGAGTGCTTG ATAACATGGG CTCATCCTGT AGCAGATCTC      4200

ATTCTTTAAG TGAGGCTGAA ACAACAAAAA ATGCAAAAGT AAGTTAGCAC TCGGACTTAC      4260

TGAACAAGTA AATGCTAACT CAATTCTTGA TTTGAGAGTT GCCACATTTG GTTTCTTCTA      4320

ATTCAGCTGG TAACAGTCTG CAGACATTGA CAGGCGAATT TTGCAAGAGA CAAAAGCAGA      4380

GCAACACATC CACAAGCTCT TACTTCTTGG TATTGCTAAC TTTCCCAAAT TTAAGTGGTC      4440

ATTTTCCTTG TCACAATTAT CTGCGCTACC TTTAGTATCT ATTGGTGGAG AAAATTAATT      4500

GTTTCTGTTG TTCCTATTTA CCTCTATAAA AAACCTTTC TCATGTTATT CCAAAAAAA      4560

AAGAAGATAA ATAAATGTAT CCTAGAAAAT TTTAGTTTGA ACTTGTTCTC AATGTGGATC      4620

CATCCTTCTT TCTCTCTCTC AATTGCTTCT GTTTTAAGGT GCGGCAGAAT CAGGGAAGTC      4680

TACGATATTT AAACAGGTGA TGAATGTTAT ATTCCATGGA GAATCATAAC CCGTACGCCG      4740

CTAGTTAGTC TGATGTATTC TTACTGTTCA CCTGCAGATT AAGCTCCTTT TCCAAACTGG      4800

CTTTGATGAG GCAGAACTTA GGAGCTACAC ATCAGTTATC CATGCAAACG TCTATCAGAC      4860

AATTAAAGTA TGCAATACTG GAAAGGGTGT GTCTTTTTTT TCTTATTGCA AAGTGGGAT      4920

TATGTAGGAG AGTCGACTAG GGATTTGTAT TCTGTTCATA AGGAAATGCG TTCATACTTT      4980

TCCTTTTTGT CGAGTAATGT GTTAAATGTT AACAGATACT ATATGAAGGA GCAAAAGAAC      5040

TCTCACAAGT GGAATCAGAT TCCTCAAAGT ATGTTATATC CCCAGATAAC CAGGTTTGTC      5100

CTTACTCTTT ACTCAACAGT TAAAGCTAAA TCTGTGCATA TGAACATGTC TTGTTAAATC      5160

TGGGAATACA AACATTTTGA TTTGCAACAT TTCTGTTGTA GTCAAGCTGC TCGGCTCTAT      5220

GTTTTAACCT GTTAAGACCT TGTAGACTGT GCTCGGCTCT ATTGTAGTCT TATATTTTAC      5280

ACGGTCATTC TATAATGAAA ACTTGAAAAA GATATCTATT GAACCGTTCA ATGTACTGAA      5340
```

```
CAAAGTAGAA AAGAACAATG AGATTTTGTA ACATTTATTC TTCCTTGTTT ATTTGATTGC   5400

TTCAGACAAT TGTTGATATG CTAAAAATAA CTTGGTATCA AATGTGGGTG TTATAAGATT   5460

CAATTTTTTC CTCAACCAGG TTAAAAAAAG TATACCTTTG TGCATTTCCC TGGTTCCGTT   5520

GCTTTGGAAC TTTAAAGGAA AACTGACTTT CCTTAGGCAT TGAAAGACAA ATATCACCAG   5580

TTTCACACTG TACACCTTAC CAACCAATTT GGTTTCTTAG ATGTCATTTA CTTTGTCATA   5640

TCATCAGGAA ATTGGAGAAA AACTATCAGA TATTGATGGC AGGTTGGATT ATCCACTGCT   5700

GAACAAAGAA CTTGTACTCG ATGTAAAAAG GTTATGGCAA GACCCAGTCA TTCAGGTGAA   5760

AACAAATAGC CATTCAAATC TTTTGAAGTT ATATAGTTTT CCTGGCCAGG TGTGCTGAAG   5820

CAATGCTCTA TACTGTAGGA AACTTACTTA CGTGGAAGTA TTCTGCAACT TCCTGATTGT   5880

GCACAATACT TCATGGAAAA TTTGGTTCGA TTAGCCGAAG CAGGTTATGT GCCAACAAAG   5940

GTGTGCTGTC CATGTTCATA GACAATTATT TACATATTCT CAGATATTTG TCCTGACACC   6000

ATTTCATGTT GATTTTAAGT CTACTTAGTC AGAGGTTGTC AAATGGTTAA CTATGTGTAC   6060

TGAGTCAGAG GTTGCCAAAT AGTTTTAAAA GATGGGCATA TGTTTATCCT TATCTTTTAA   6120

ATAATATTGG AGGCTATCCT TTAAAATTCA ATATTAGGGA GGAGAAACTA TTATTCTACC   6180

GTTATTACGC AGTCTACATA ACGAAGGTAA AAAATGTCCC TGTGAAACAT AGGGTGCAAA   6240

ACTACTGTGA ATAAAACTCT ACTTATCTAA GCACCTTGAG CTTTTGAGTT CCCACATATT   6300

AATCTTATGA CACTAGCATA TATTTTTTTT GTTCAGTTCC TTCAATAAGT TGCAAACCAC   6360

AAATATGATC ACTGTACCAT CCACTTTTGC AACCATTTCC CGTCATTTCT TAAGCATAGA   6420

AAATTGTTTG TCACTTGTTT AAGTCCACAC TGCATGAAAA TTCCAATTAA CTTTGTGTGC   6480

TAAGTGAAGA TATGACTCCA TATTTCTGCA TTTAGCAGTC TGGATGGGAT AATTTGTGAT   6540

TGTACCTTGT CTAATGGTTC GTTTGAAAGG CTGGTAGTTG ATCTTCCATA CTTAAGAATG   6600

CTTGCAGTAT TATAGTTGTC AATATTATGA GTCATTTTCC AGGAGGATGT GCTTTATGCA   6660

AGAGTACGGA CAAATGGTGT TGTACAAATA CAATTTAGGT AATCTGCTGA CACTATTTTT   6720

TGCACATTTT TTTGCTGGTT GCTCTACTAT GTACAGAACG ACAAGTTGAA GTCCTTTTTT   6780

CCTCCCTTTT CACTTCTAAG ATATGACCTG AGAGGTTCTG AATGTAGCTG TTATAAGATG   6840

AGTTGAATCA TCTAGTTAAC TGGGTTTCTT TCTGCAGTCC TGTTGGAGAA AACAAAAGAG   6900

GTGGAGAGGT ATATAGGTTG TATGATGTAG GAGGCCAGAG GAATGAGAGG AGAAAGTGGA   6960

TTCATCTTTT TGAAGGTGTT AATGCGGTAA TCTTTTGTGC TGCCATTAGC GAGTAAGTAC   7020

AATTTTTTTG ATTGTTGAAC TTATCCTAAT CTGCTAAGTT CTTCTCATAG GCTTCTTGTT   7080

CATTTCAGAT ATGATCAGAT GCTATTTGAA GATGAGACAA AAAACAGAAT GATGGAGACC   7140

AAGGAACTCT TTGACTGGGT TTTAAAGCAA AGATGTTTTG AGGTCTGCAT GCATCCATTT   7200

CTGCAACCTT TGTGCTCATG CTTTTTTTTC TCATTTTGAA ACTAATTACG GTGCTATATT   7260

GACCATCAGA AAACATCATT CATTCTGTTT CTCAACAAAT TTGATATATG CGAGAAGAAA   7320

ATACAAAAGG TAAGGCCTGC TCTTTGTACC AATGCATAGT TTAGTACTAA ATGTTACCAA   7380

CATTTATGTT TTCGCTGGTT ACGTAGGTTC CTTTAAGTGT GTGCGAGTGG TTTAAAGACT   7440

ACCAGCCTAT TGCACCTGGG AAACAGGAGG TTGAACATGC ATATGAGTGA GTCCACTACT   7500

CGCCCTCTCA GATGAACATG GGCATTTGGC CATTTGTAAT GTTGCTGCAT GGTGCACTTA   7560

TATGCCTTGA TAAGTTTTTC CATTCTAATG TTATATAGTA TCAAACGTTC ATCATTACTG   7620

TGGCTTATGG TCTGGAGTGA CGTTTTACAG GTTTGTCAAG AAGAAGTTTG AAGAGCTCTA   7680
```

-continued

```
CTTCCAGAGC AGCAAGCCTG ACCGTGTGGA CCGCGTCTTC AAAATCTACA GAACTACGGC    7740

CCTAGACCAG AAACTTGTAA AGAAGACATT CAAGTTGATT GATGAGAGCA TGAGACGCTC    7800

CAGGGAAGGA ACTTGATTCA GAGCTAAGAC TAGGTTGTAA GTCACACAGG GAAGGTAATT    7860

AGGACGGCGA GAGGAACAAA GTTTCACACT GTCACAGCTT TATCTGTTGT AATTCTTTTA    7920

CACGTGGACC ATTGATTGAC CTTTTGGTTC TTACTGTGGG CTGTTCAGGT CTGTACCCTA    7980

TTTTTTGTTC TCTAGTTAGC CATTGTGCAA ATTTTCCTTG AATCAGATTC TCTACCTGTT    8040

GTCTATGTGT GTTATCTTGG TCTGTTAATT TGCATAGCCC ACTTGTTACA AAAGGAGAGC    8100

CGAATTC                                                             8107
```

METHOD OF DWARFING PLANTS

FIELD OF THE INVENTION

The present invention relates to a method of dwarfing plants and a molecule used in said method.

BACKGROUND OF THE INVENTION

Miniaturizing plants is important from various aspects of agriculture and horticulture. For example, miniaturizing the plant height or the culm length can produce ornamental plants with new aesthetic values, and miniaturizing vegetables or fruits can create crops having new commercial values such as being bite-sized. Aside from these industrial applications, miniaturizing experimental plants will not only make them easy to handle but will also reduce the space necessary for culturing the plants, which leads to efficient use of the laboratory space.

In plant miniaturization, the characteristic that reduces the plant height or the culm length compared to the wild type (the normal type) is called dwarfism. A number of strains and varieties of rice having this characteristic have been produced by γ-ray or chemical mutagenesis, and they have been genetically analyzed for a long time. Over 60 different genes have so far been found to be involved in dwarfism (Rice Genetic Newsletter, 12: 30–32 (1995)). However, little is known about why the dwarf phenotype is expressed, except that a few dwarf mutants are caused by mutations at the genes involved in the biosynthesis of gibberellin, which is a plant growth hormone.

Among the dwarf mutants of rice, the Daikoku type dwarfism is known for suppressing the elongation of the second internode, thereby reducing the plant height to less than one half of the normal, and rendering the grain small and circular (Masao Akemine, Nihon Gakujutsukai Houkoku (Japan Science Council Report), 1: 108–314 (1925), Tsutsumu Nakayama, Shinshudai Bunrigakubu Kiyou (Journal of Faculty of Liveral Arts and Science Shinshu University), 4: 1–31 (1954); Man-emon Takahashi and Kazuyoshi Takeda, Hokudai Nou Houbun Kiyou (Memories of the Faculty of Agriculture Hokkaido University), 7: 32–43 (1969)). Furthermore, genetic analysis has clarified that the Daikoku type dwarfism is regulated by a single recessive gene, d1, on rice chromosome 5 (Nagao and Takahashi, J. Fac. Agr., Hokkaido Univ. 53: 72–130 (1963); Iwata and Omura, Jpn. J. Genet. 51: 135–137 (1976)). In d1 gene mutants, the plant hormone gibberellin contents are high enough to be equal to the normal type, and the plant height cannot be recovered to normal by exogenous gibberellin treatments (Suge, H. and Y. Murakami, Plant and Cell Physiol. 9: 411–414 (1968)). This characteristic suggests that the d1 gene is not involved in the biosynthesis of gibberellin within the plant body, but is presumedly involved in a genetic locus associated with the gibberellin receptor molecule or the signal transduction thereafter (Mitsunaga, S., Tashiro, T. and Yamaguchi, J., Theor. Appl. Genet. 87: 705–712 (1994)).

Therefore, it is important to isolate the Daikoku type dwarfism gene d1 and to reveal the function of its gene product not only to clarify the morphogenesis in plants but also to artificially control the plant sizes utilizing the knowledge obtained.

SUMMARY OF THE INVENTION

An objective of the present invention is to isolate the d1 gene which is involved in dwarfism of plants. Another objective of the present invention is to provide a method of dwarfing plants by controlling the expression of the d1 gene and to provide a molecule to control the expression of the d1 gene.

Rice dwarfism gene d1 has so far been known to encode a protein associated with dwarfism of rice and to exist at a certain locus in the vast region of rice chromosome 5. In order to isolate the d1 gene from the vast chromosomal region, the present inventors determined the location of the d1 gene using a linkage analysis and succeeded in isolating the desired gene by the map-based cloning method. More specifically, the region on the chromosome where the d1 gene is located was narrowed to a region between specific molecular markers by linkage analysis. A physical map of the area around the region thus narrowed was then made by aligned YAC clones. As a result of EST mapping, the inventors succeeded in identifying a single cDNA clone "ST5933" on these YAC clones as the candidate for the d1 gene.

The nucleotide sequence of isolated clone ST5933 (362 base pairs) was analyzed by a homology search for the gene sequence in the database. This gene was characterized as the α subunit of a G protein in plants. However, this gene has not previously been associated with plant dwarfism thus far.

G proteins are known to function as the receptors for hormones or the factors involved in signal transduction from the receptors in living organisms including humans. Rice dwarfism gene d1 may also be a receptor for the plant hormone gibberellin or be involved in the signal transduction thereafter. G protein genes that have functions similar to those described above are expected to exist not only in rice plants but also widely in the plant kingdom. The present inventors have found that a wide variety of plants can be dwarfed by repressing the expression of the d1 gene or its homologous genes in other plants.

Thus, the present invention relates to a method of dwarfing plants by repressing the expression of the d1 gene or its homologues, which is associated with the dwarfism of plants, and to a molecule used to repress the expression of the genes. More specifically, it relates to (1) a DNA for dwarfing plants encoding an antisense RNA complementary to the transcription product of the DNA of (a), (b), or (c) below:
  (a) a DNA encoding a protein comprising the amino acid sequence described in SEQ ID NO: 1;
  (b) a DNA comprising the nucleotide sequence described in SEQ ID NO: 2; or
  (c) a DNA which hybridizes with the DNA comprising the nucleotide sequence described in SEQ ID NO: 2, and encodes a protein functionally equivalent to a protein comprising the amino acid sequence described in SEQ ID NO: 1;
  (d) a DNA encoding the amino acid sequence of SEQ ID NO: 1 comprising one or more conservative amino acid substitutions
(2) a DNA for dwarfing plants encoding an RNA having ribozyme activity to specifically cleave the transcription product of the DNA described in (a), (b), or (c) of (1);
(3) a DNA for dwarfing plants encoding an RNA which represses the expression of the DNA described in (a), (b), or (c) of (1) in the plant cell through a co-repressive effect;
(4) use of the DNA of (1), (2), or (3) for dwarfing plants;
(5) a method of dwarfing plants, which comprises repressing the expression of the DNA described in (a), (b), or (c) of (1) in a plant cell;
(6) the method of (5), wherein the expression of the DNA described in (a), (b), or (c) of (1) is repressed by expressing the DNA of (1), (2), or (3) in the plant cell;

(7) a method of dwarfing plants, which comprises:
(a) introducing a substance that represses the expression of the DNA described in (a), (b), or (c) of (1) into the plant cells; and
(b) regenerating said plant cells to obtain transgenic plants;
(8) The method of (7), wherein said substance is the DNA of (1), (2), or (3);
(9) a transformed plant cell retaining the DNA of (1), (2), or (3) and capable of expressing said DNA;
(10) a dwarf transgenic plant containing the cell of (9); and
(11) a reproductive media of the plant of (10).

DETAILED DESCRIPTION OF THE INVENTION

Figure 1:
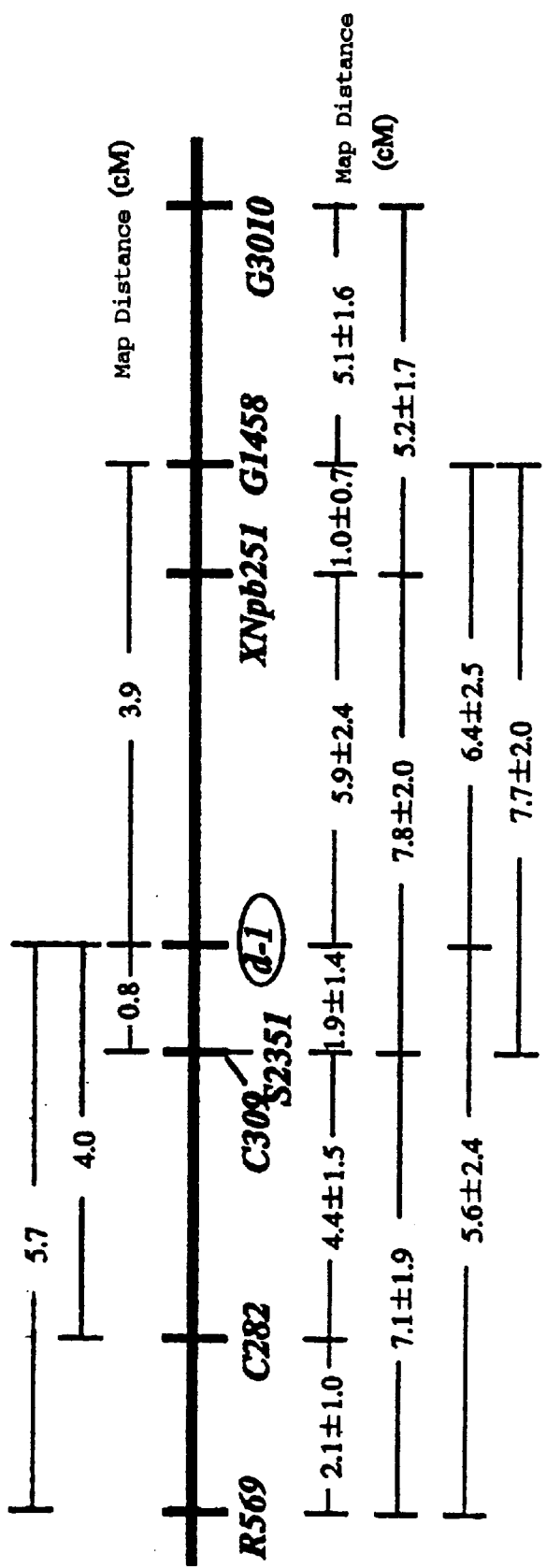
FIG. 1 shows the inferred region for the d1 locus based on crude scale linkage analysis.

The present invention relates to a method of dwarfing plants by repressing the expression of the d1 gene or its homologues, and to a molecule that represses the expression of these genes. SEQ ID NO: 2 shows the nucleotide sequence of the CDNA of the d1 gene (the present inventors have clarified how this gene is involved in rice dwarfism), SEQ ID NO: 3 shows the nucleotide sequence of its genomic DNA, and SEQ ID NO: 1 shows the amino acid sequence of the protein encoded by these DNAs. (These sequences are referred to in Seo et al., Plant. Mol. Biol. 27: 1119–1131 (1995) and Ishikawa et al., Plant. Cell. Physiol. 36(2): 353–359 (1995).)

The d1 gene has so far been known to give the dwarf phenotype to the rice plant and exists at a locus somewhere within the vast region of rice chromosome 5. The present inventors narrowed the region where the d1 gene exists on rice chromosome 5 by means of the map-based cloning method, and ultimately succeeded in identifying it as a single gene. This gene was isolated and characterized as a gene encoding the a subunit of the G protein trimer which is involved in intracellular signal transduction (Seo et al., Plant. Mol. Biol. 27: 1119–1131 (1995); Ishikawa et al., Plant. Cell. Physiol. 36(2): 353–359 (1995)), and we are the first to prove its relationship with plant dwarfism. The results of northern hybridization indicated that the d1 gene is expressed in the wild type but not in the d1 mutant strains (Example 5). Based on these data, the present inventors found that the dwarf phenotype can be induced in plants by repressing the expression of the d1 gene.

The target gene of the present invention, whose expression is repressed in order to dwarf plants, is not limited to the rice d1 gene. Any gene, in addition to the rice d1 gene, derived from other plants can be used as the target gene as long as it encodes a functionally equivalent protein. The term "functionally equivalent protein" means a G protein, other than the protein encoded by the d1 gene, the repression of whose expression induces the plant dwarfism. Rice dwarfism gene d1 encodes the α subunit of the trimeric G protein trimer, which suggests its possible association with the receptor for the plant hormone gibberellin or with the signal transfer thereafter. Therefore, it is reasonable to infer that its homologous genes exist not only in rice plants but also widely in the plant kingdom. The present invention enables dwarfing plants other than rice utilizing these homologous genes. The target plants to be dwarfed in the present invention include wheat, barley, corn, tomato, pea, and soybean but are not restricted thereto.

Genes encoding the proteins functionally equivalent to the protein encoded by the rice d1 gene can be isolated by methods well known to persons skilled in the art. These include the hybridization technique (Southern, E. M., J. Mol. Biol. 98: 503 (1975)) and the polymerase chain reaction (PCR) technique (Saiki, R. K. et al., Science 230: 1350–1354 (1985); Saiki, R. K. et al., Science 239: 487–491 (1988)). Namely, a person skilled in the art could routinely isolate genes homologous to the d1 gene from plants other than rice by using the nucleotide sequence of the rice d1 gene (SEQ ID NO: 2) or part thereof as the probe, and using oligonucleotides that hybridize specifically with the d1 gene (SEQ ID NO: 2) as the primers.

In the present invention, a plant can be dwarfed by repressing the expression of the plant endogenous d1 gene or its homologues. The phrase "repression of gene expression" in the present invention includes repression of the gene transcription and repression of the translation into protein. It also includes not only the complete inability of gene expression but also reduction of expression.

The expression of a specific endogenous gene in plants can be repressed by methods utilizing the antisense technology, which are most commonly used in the art. Ecker et al. were the first to demonstrate the antisense effect of an antisense RNA introduced by electroporation in plant cells by using the transient gene expression method (J. R. Ecker and R. W. Davis, Proc. Natl. Acad. Sci. USA 83: 5372 (1986)). Thereafter, the target gene expression was reportedly reduced in tobacco and petunias by expressing antisense RNAs (A. R. van der Krol et al., Nature 333: 866 (1988)). The antisense technique has now been established as a means to repress the target gene expression in plants. Multiple factors are required for antisense nucleic acid to repress the target gene expression. These include inhibition of transcription initiation by triple strand formation, repression of transcription by hybrid formation at the site where the RNA polymerase has formed a local open loop structure, transcription inhibition by hybrid formation with the RNA being synthesized, repression of splicing by hybrid formation at the junction between an intron and an exon, repression of splicing by hybrid formation at the site of spliceosome formation, repression of mRNA translocation from the nucleus to the cytoplasm by hybrid formation with mRNA, repression of splicing by hybrid formation at the capping site or at the poly A addition site, repression of translation initiation by hybrid formation at the binding site for the translation initiation factors, repression of translation by hybrid formation at the site for ribosome binding near the initiation codon, inhibition of peptide chain elongation by hybrid formation in the translated region or at the polysome binding sites of mRNA, and repression of gene expression by hybrid formation at the sites of interaction between nucleic acids and proteins. These factors repress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society), Tokyo Kagaku Dozin, pp. 319–347, (1993)). The antisense sequence used in the present invention can repress the target gene expression by any of the above mechanisms. In one embodiment, it will effectively inhibit translation of a gene if an antisense sequence is designed to be complementary to the untranslated region near the 5' end of the gene's mRNA. It is also possible to use sequences complementary to the coding regions or to the untranslated region on the 3' side. Thus the antisense DNA used in the present invention includes DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous d1 gene (or its homologue) of the plant to be transformed or a part thereof, but it need not be perfectly complementary as long as it can effectively inhibit the gene expression. The transcribed RNA is preferably at least 90%, and most preferably at least 95% complementary to the transcribed products of the target gene. In order to effectively inhibit the expression of the target gene by means of an antisense sequence, the antisense DNA should be at least 15 bases long, more preferably at least 100 bases long, and still more preferably at least 500 bases long. The antisense DNA to be used is generally shorter than 5 kb, and preferably shorter than 2.5 kb.

DNA encoding ribozymes can also be used to repress the expression of endogenous genes. A ribozyme is an RNA molecule that has catalytic activities. There are many ribozymes having various activities. Research on the ribozymes as RNA cleaving enzymes has made it possible to design a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Makoto Koizumi and Eiko Ohtsuka, Tanpakushitsu Kakusan Kohso (Nucleic acid, Protein, and Enzyme), 35: 2191 (1990)).

The self-cleavage domain of a hammerhead type ribozyme cleaves at the 3' side of C15 in G13U14C15. Formation of a nucleotide pair between U14 and A at the ninth position is considered important for the ribozyme activity. Furthermore, it has been shown that the cleavage also occurs when the nucleotide at the 15th position is A or U instead of C (M. Koizumi et al., FEBS Lett. 228: 225 (1988)). If the substrate binding site of the ribozyme is designed to be complementary to the RNA sequences adjacent to the target site, it is possible to create a restriction-enzyme-like RNA cleaving ribozyme which recognizes the sequence UC, UU, or UA within the target RNA (M. Koizumi et al., FEBS Lett. 239: 285 (1988); Makoto Koizumi and Eiko Ohtsuka, Tanpakushitsu Kakusan Kohso (Protein, Nucleic acid, and Enzyme), 35: 2191 (1990); M. Koizumi et al., Nucleic Acids Res. 17: 7059 (1989)). For example, there are more than 100 sites that can be used as the target in the coding region of the d1 gene (SEQ ID NO: 2).

The hairpin type ribozyme is also useful in the present invention. A hairpin type ribozyme can be found, for example, in the minus strand of the satellite RNA of tobacco ringspot virus (J. M. Buzayan, Nature 323: 349 (1986)). This ribozyme has also been shown to target-specifically cleave RNA (Y. Kikuchi and N. Sasaki, Nucleic Acids Res. 19: 6751 (1992); Yo Kikuchi, Kagaku To Seibutsu (Chemistry and Biology) 30: 112 (1992)).

The ribozyme designed to cleave the target is fused with a promoter such as the cauliflower mosaic virus 35S promoter and with a transcription termination sequence, so that it will be transcribed in plant cells. However, if extra sequences have been added to the 5' end or the 3' end of the transcribed RNA, the ribozyme activity might be lost. In this case, one could place an additional trimming ribozyme, which functions in cis to perform the trimming on the 5' or the 3' side of the ribozyme portion, in order to precisely cut out the ribozyme portion from the transcribed RNA containing the ribozyme (K. Taira et al., Protein Eng. 3: 733 (1990); A. M. Dzaianott and J. J. Bujarski, Proc. Natl. Acad. Sci. USA 86: 4823 (1989); C. A. Grosshands and R. T. Cech, Nucleic Acids Res. 19: 3875 (1991); K. Taira et al. Nucleic Acid Res. 19: 5125 (1991)). Multiple sites within the target gene can be cleaved by arranging these structural units in tandem to achieve greater effects (N. Yuyama et al., Biochem. Biophys. Res. Commun. 186: 1271 (1992)). By using such ribozymes, it is possible to specifically cleave the transcription products of the target gene in the present invention, thereby repressing the expression of said gene.

Endogenous gene expression can also be repressed by co-repression through the transformation by DNA having a sequence identical or similar to the target gene sequence. "Co-repression" refers to the phenomenon in which, when a gene having a sequence identical or similar to the target endogenous gene sequence is introduced into plants by transformation, expression of both the introduced exogenous gene and the target endogenous gene becomes repressed. Although the detailed mechanism of co-repression is unknown, it is frequently observed in plants (Curr. Biol. 7: R793 (1997), Curr. Biol. 6: 810 (1996)). For example, if one wishes to obtain a plant body in which the d1 gene is co-repressed, the plant in question can be transformed with a vector DNA designed so as to express the d1 gene or DNA having a similar sequence to select a plant having the d1 mutant character, i.e., a dwarf plant, among the resultant plants. The gene to be used for co-repression does not need to be completely identical to the target gene, but it preferably has at least a 90% sequence identity.

In addition, endogenous gene expression in the present invention can also be repressed by transforming the plant with a gene having the dominant negative phenotype of the target gene. A gene having the dominant negative phenotype means a gene which, when expressed, can eliminate or reduce the activity of the wild type endogenous gene inherent to the plant. The d1 gene used in the present invention is known as the α subunit of a heterotrimeric G protein. In general, if a mutant protein, in which mutations are introduced into the regions important for GTP/GDP binding activities or GTPase activities in the α subunit, is expressed, and the regions important for heterotrimer formation and receptor binding are left the same as the wild type, the protein will have a dominant negative phenotype because it forms complexes with the other subunits and the receptor but is not activated by GTP. For example, an amino acid sequence (-Asp-Val-Gly-Gly-Gln-), which is well-conserved in the α subunit of a G protein, is considered to be the site that interacts with the phosphate group on the γ position of GTP. It has been shown, for example, that a mutant protein of the α subunit of a G protein, in which the first Gly in the above amino acid sequence has been replaced with Thr, exhibits a dominant negative phenotype when expressed in the COS-1 cells (J. Biol. Chem. 266: 4673 (1991)). In a plant transformed to express dominant negative proteins having the above mutations, the target gene is considered to be functionally inhibited.

The substance to be used for dwarfing plants of the present invention is not particularly limited, as long as it represses the expression of the plant endogenous d1 gene or its homologues in the plant cells.

The transformed dwarf plant body can be produced by introducing said substance into plant cells and regenerating the transformed plant cells. The substance includes the above-mentioned DNAs.

When said substance is a DNA that can repress gene expression, the DNA is inserted into an appropriate vector, the vector is introduced into plant cells, and the transformed plant cells are regenerated. Any vector which enables expression of the inserted gene in plant cells can be used. For example, vectors having a promoter for constitutive gene expression in plant cells (such as the 35S promoter of cauliflower mosaic virus) can be used. Also, if a tissue-specific promoter of plants is used, it may be possible to achieve tissue-specific dwarfism, e.g., dwarfing specific parts of the plant such as leaves, flowers, and fruit. The tissue-specific promoters include seed-specific promoters such as the kidney bean β-phaseolin gene (Bustos et al., EMBO J. 10: 1469–1479 (1991)) and the soybean glycinin gene (Lelievre et al., Plant Physiol. 98: 387–391 (1992)), leaf-specific promoters such as the pea RbcS gene (Lam and Chua, Science 248: 471–474 (1990)) and the wheat Cab1 gene (Gotorn et al., Plant J. 3: 509–518 (1993)), and root-specific promoters such as the tobacco TobRB7 gene (Yamamoto et al., Plant Cell 3: 371–382 (1991)) and the Agrobacterium rhizogenes rolD gene (Elmayan and Tepfer, Transgenic Res. 4: 388–396 (1995)). Vectors having a promoter that is activated by exogenous stimuli can also be used. Any plant cell can be used as plant cells into which such a vector is introduced, including wheat, barley, corn, tomato, soybean, rapeseed, poplar, and apple, as well as rice. The plants can be any coniferous trees, broad-leaved trees, dicotyledons, or monocotyledons. The phrase "plant cells" as used herein includes various forms of plant cells such as suspension culture cells, protoplasts, leaf sections, and calluses. The vector can be introduced into plant cells by various methods well known to persons skilled in the art, such as the polyethyleneglycol method, electroporation, the Agrobacterium-mediated method, and the particle gun method. The plant body can be regenerated from the transformed plant cells by methods well known to persons skilled in the art depending on the types of the plant cells (Toki et al., Plant Physiol. 100: 1503–1507 (1995)).

The target gene expression in the plant body thus produced or that obtained from its reproductive media (e.g., seed, tuber, ear, etc.) is repressed as compared with that in the wild type plant. The plant body is thus dwarfed. The dwarfism of plants in the present invention includes the dwarfism of not only the whole plant body but also part of the plant body.

Furthermore, the plant growth may be augmented by introducing the rice d1 gene we isolated or a homologous gene from other plants into a wild type plant, and expressing the introduced gene. Specific examples of the gene to be introduced into the plant cells include (1) a DNA encoding a protein consisting of the amino acid sequence described in SEQ ID NO: 1;

(2) a DNA encoding a protein having a modified amino acid sequence described in SEQ ID NO: 1 in which one or more amino acids are substituted, deleted, or added, and functionally equivalent to the protein consisting of the amino acid sequence described in SEQ ID NO: 1;

(3) a DNA containing the coding region of the nucleotide sequence described in SEQ ID NO: 2; and (4) a DNA which hybridizes complementarily to the DNA having the nucleotide sequence described in SEQ ID NO: 2, and which encodes a protein functionally equivalent to the protein consisting of the amino acid sequence described in SEQ ID NO: 1.

The vectors used to express the gene in the plant cells, the plant cells into which the vectors are introduced, and the methods of regenerating the plant body can be the same as those described above in dwarfing plants.

The present invention provides a method of dwarfing plants by repressing the expression of the rice d1 gene, which is involved in dwarfism, or its homologues in other plants. This method enables, for example, creating ornamental plants and agricultural products with new commercial values, and therefore is especially useful in the areas of agriculture and horticulture.

The following examples demonstrate the present invention in more detail, but are not to be construed to limit the scope of the present invention.

EXAMPLE 1

Crude Scale Linkage Analysis of the Dwarf Gene d1

An F2 population, consisting of 100 individual plants produced by crossing an Indica type variety IR24 with a Japonica type genetic marker line FL2, having the d1 gene, was grown, and DNA from each individual plant was extracted. Since it was known that d1 is located on chromosome 5, a linkage analysis between the d1 gene and RFLP markers located on chromosome 5 was performed to produce a linkage map. In order to determine the location more precisely, a linkage analysis using the pooled sampling method (Churchill et al., Proc. Natl. Acad. Sci. USA 90: 16–20 (1993)) was then performed. Namely, a BC3F2 population consisting of about 2,600 individual plants obtained by backcrossing the genetic marker line FL2 with IR24 as the recurrent parent was selected at the juvenile seedling stage, and 644 dwarf individuals (recessive homozygotes) were grown. An RELP analysis was performed for this population using the markers near the d1 gene to produce a more precise linkage map. The results revealed that the d1 gene is linked with RFLP markers C309 and S2351 at a frequency of about 0.8% (FIG. 1). However, most of the DNA markers presumed to be located near the d1 gene did not show polymorphism between the parental strains of segregating populations used. Thus, the population to be analyzed was changed.

EXAMPLE 2

Preparation of a Fine Scale Linkage Map of the Dwarf Gene d1

Figure 2:
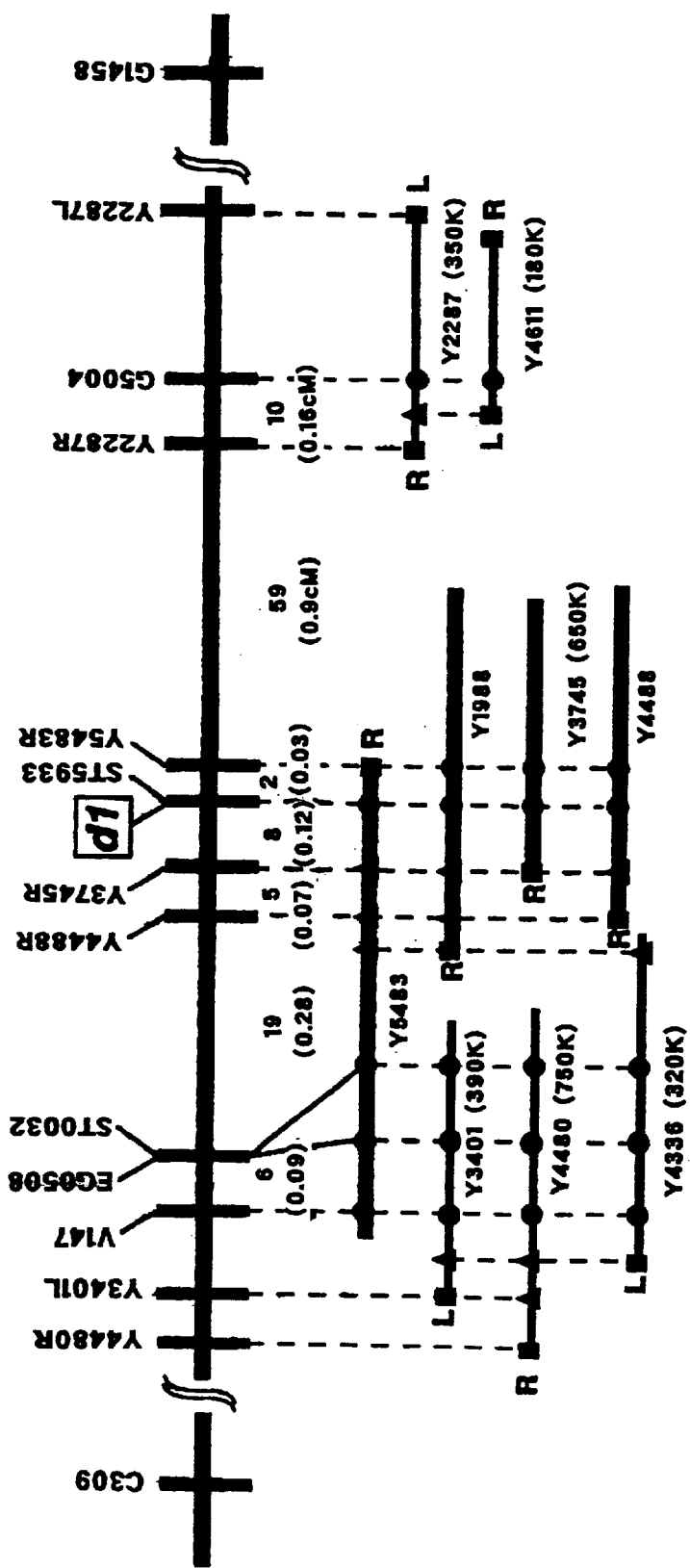
FIG. 2 shows the inferred region for the d1 locus based on fine scale linkage analysis.

In order to obtain the polymorphism of DNA markers more certainly, we selected SL18 as the parent strain for the segregating populations. This strain has the genetic background (12 kinds of chromosomes) of the Nipponbare except that chromosome 5 has been substituted by that of the Kasalath. About 13,000 of the F2 seeds obtained by crossing SL18 and FL2 were sowed, and 3185 dwarf plants (recessive homozygotes) were selected and transplanted in the field at the juvenile seedling stage. Leaves were sampled by grouping every five individuals in one pool, and the DNA was extracted from 637 pools and subjected to RFLP analysis. The results indicated that 37 pools contained recombinant individuals between d1 and RFLP marker V147 which is positioned near the d1 locus on chromosome 5, and that 71 pools contained recombinant individuals between d1 and G5004. Based on these results, the d1 locus was presumedly in the region (1.8 cM) between V147 and G5004 (FIG. 2). In order to identify the recombinant individuals from the pools containing recombinants, DNA was extracted from 540 individuals (5 individuals×108 pools), and the individuals in which recombination occurred between d1 and V147 or between d1 and G5004 were selected by RFLP analysis.

EXAMPLE 3

Selecting the YAC Clones Containing the Dwarf Gene d1 and Preparing the Alignment Map of these Clones A YAC library was screened using V147 and G5004 in order to identify a genomic clone containing the d1 locus (Umehara et al., Molecular Breeding 1: 79–89 (1995)). As a result, three YAC clones containing the nucleotide sequence V147 and two containing the sequence G5004, were selected. DNA fragments were prepared by the cassette-PCR method. By using the DNA fragments corresponding to both ends of each YAC clone, we were able to confirm overlaps among YAC clones, perform chromosome walking, and map clones onto the linkage map. It was found that one end clone of Y5483, Y5483R, was linked to the d1 locus by as close as 0.03 cM, and that it was mapped between the d1 locus and G5004. These results indicated that this YAC clone contained the d1 locus. Furthermore, when YAC clones were selected again using the end DNA fragment of the above YAC clone, three new YAC clones (Y1988, Y3745, and Y4488) were obtained. The overlap among these YAC clones was examined by hybridization or the PCR method, and four different YAC clones were found to contain the d1 gene.

EXAMPLE 4

Identification of the Candidate Gene for the Dwarf Gene d1

EST mapping (direct positioning of cDNA clones against the YAC clones) is being performed in the Rice Genome Research Program. This program includes investigating the presence of CDNA clones corresponding to the above YAC clone. Based on the information accumulated thus far, ST5933 was found to be located on the YAC clone, Y5483. Using this clone as a probe, an RFLP analysis was performed by means of the genomic southern hybridization for the recombinant individuals near d1 specified by the fine scale linkage analysis. The results revealed that the 9.6 kb band (Nipponbare) coming from ST5933 co-segregates with the d1 gene (FIG. 2).

Figure 3:
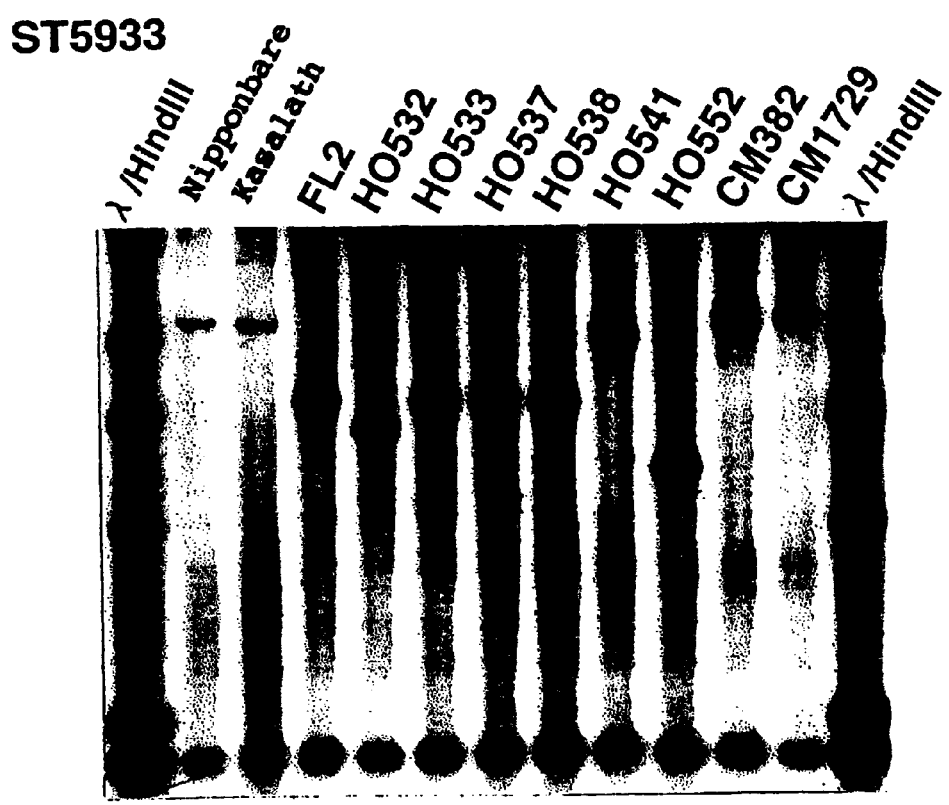
FIG. 3 represents an electrophoretic image showing the results of the genomic Southern hybridization of two wild type varieties (Nipponbare and Kasalath) and nine d1 mutants (FL2, HO532, HO533, HO537, HO538, HO541, HO552, CM382, and CM1792) using ST5933 as a probe. The samples were electrophoresed on a 0.8% agarose gel and blotted onto a nitrocellulose membrane. The signal was detected by an ECL system.

A genomic southern hybridization of d1 mutant strains was then performed using the molecular marker ST5933 as a probe (FIG. 3). Consequently, a band of approximately 9.6 kb was found in the two kinds of the normal rice variety, Nipponbare (Japonica) and Kasalath (Indica), but bands having the sizes different from the normal rice variety were detected in seven of the nine d1 mutant strains(FL2, HO532, HO533, HO537, HO538, HO541, and HO552). In general, RFLP is rather frequently found between Nipponbare and Kasalath, but polymorphism among japonica varieties is very rarely detected. However, these results revealed polymorphism among the d1 mutant strains having a genetic background of the japonica variety. This indicates that considerable structural variations exist in the genomic DNA region of the candidate gene ST5933 among the d1 mutant strains. This suggested that ST5933 is a promising candidate for the d1 gene. The results of homology search indicated that ST5933 encodes the α subunit of a trimeric G protein, whose cDNA and the genomic DNA region had already been isolated, and whose structure (nucleotide sequence) had been analyzed (Seo et al., Plant Mol. Biol. 27: 1119–1131 (1995); Ishikawa et al., Plant Cell. Physiol. 36 (2): 353–359 (1995)).

EXAMPLE 5

Analysis of the Expression Pattern of ST5933

Figure 4:
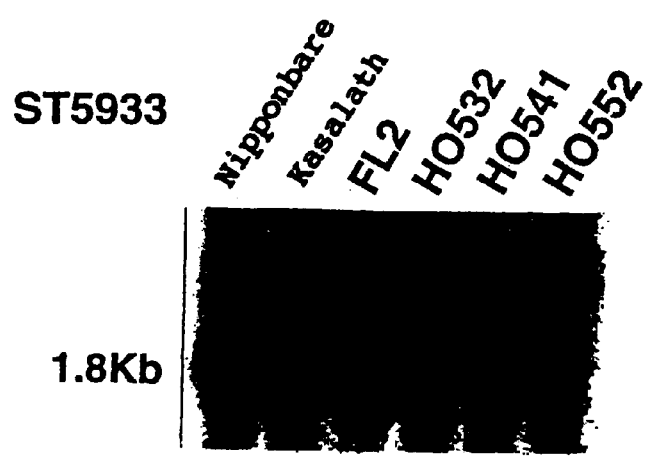
FIG. 4 represents an electrophoretic image showing the results of the northern hybridization of two wild type varieties (Nipponbare and Kasalath) and four d1 mutants (FL2, HO532, HO541, and HO552) using ST5933 as a probe.

RNA was extracted from the four different d1 mutant strains having structural variations in the candidate gene ST5933 by the genomic Southern hybridization. RNA was also extracted from the two normal varieties (Nipponbare and Kasalath). Northern hybridization was then performed on both RNAs using ST5933 as a probe (FIG. 4). As a result, a 1.8 kb band was detected in the two normal varieties, but not in the four d1 mutant strains. The results support the hypothesis that the candidate gene ST5933 is a causal gene of the dwarf phenotype d1.

What is claimed is:

1. A method of producing a dwarf plant, the method comprising inhibiting expression of an RNA transcription product of SEQ ID NO:2 in said plant using an antisense oligonucleotide complementary thereto, wherein the inhibition of expression of the RNA results in the production of a dwarf plant.

2. The method of claim 1, wherein the inhibiting of expression of an RNA comprises:
   (1) introducing into a plant cell a nucleotide sequence that is transcribed into an antisense RNA oligonucleotide complementary to an RNA transcription product of SEQ ID NO:2; and
   (2) regenerating a transformed plant from the plant cell, thereby producing the dwarf plant.

3. The method of claim 2, wherein the antisense RNA oligonucleotide is from 15 bases to 2500 bases in length.

4. A method of producing a dwarf plant, the method comprising inhibiting expression of an RNA transcription product of SEQ ID NO:2 in said plant using an antisense oligonucleotide which is at least 100 bases in length and at least 90% complementary thereto, wherein the inhibition of expression of the RNA results in the production of a dwarf plant.

5. The method of claim 4, wherein the inhibiting of expression of an RNA comprises:
   (1) introducing into a plant cell a nucleotide sequence that is transcribed into an antisense oligonucleotide which is at least 100 bases in length and at least 90% complementary to an RNA transcription product of SEQ ID NO:2; and
   (2) regenerating a transformed plant from the plant cell, thereby producing the dwarf plant.

6. The method of claim 3, wherein the antisense RNA oligonucleotide is at least 100 bases in length.

7. The method of claim 6, wherein the antisense RNA oligonucleotide is at least 500 bases in length.

8. The method of claim 4, wherein the antisense RNA oligonucleotide is at least 500 bases in length.

\* \* \* \* \*

UNITED STATES PATENT AND TRADEMARK OFFICE
CERTIFICATE OF CORRECTION

PATENT NO.    : 6,501,007 B1
DATED         : December 31, 2002
INVENTOR(S)   : Motoyuki Ashikari et al.

It is certified that error appears in the above-identified patent and that said Letters Patent is hereby corrected as shown below:

<u>Title page,</u>
Item [73], Assignee, after "National Institute of Agrobiological Sciences, Ibaraki (JP)," please insert -- Society of Techno-Innovation of Agriculture, Forestry and Fisheries, Ibaraki (JP) --

Signed and Sealed this

Nineteenth Day of August, 2003

JAMES E. ROGAN
*Director of the United States Patent and Trademark Office*